United States Patent
Branden et al.

(10) Patent No.: US 6,720,310 B1
(45) Date of Patent: Apr. 13, 2004

(54) TRANSFER METHOD FOR SPECIFIC CELLULAR LOCALIZATION OF NUCLEIC ACIDS

(75) Inventors: Lars Branden, Stockholm (SE); Abdalla J. Mohamed, Kista (SE); C. I. Edvard Smith, Hagersten (SE)

(73) Assignee: Avaris AB, Stockholm (SE)

( * ) Notice: Subject to any disclaimer, the term of this patent is extended or adjusted under 35 U.S.C. 154(b) by 0 days.

(21) Appl. No.: 09/787,033

(22) PCT Filed: Mar. 15, 1999

(86) PCT No.: PCT/SE99/00398

§ 371 (c)(1),
(2), (4) Date: May 14, 2001

(87) PCT Pub. No.: WO00/15824

PCT Pub. Date: Mar. 23, 2000

(30) Foreign Application Priority Data

Sep. 13, 1998 (SE) .............................................. 9803099

(51) Int. Cl.⁷ .............................................. A61K 48/00
(52) U.S. Cl. ...................... 514/44; 435/320.1; 435/455; 435/325; 435/6
(58) Field of Search ......................... 435/6, 320.1, 325, 435/455; 424/450; 514/44

(56) References Cited

U.S. PATENT DOCUMENTS

| 5,736,392 | A | | 4/1998 | Hawley-Nelson et al. |
| 6,165,720 | A | * | 12/2000 | Felgner .......................... 435/6 |
| 6,312,956 | B1 | * | 11/2001 | Lane .......................... 435/455 |

FOREIGN PATENT DOCUMENTS

| WO | 9307883 | 4/1993 |
| WO | A1-9307883 | 4/1993 |
| WO | 9319768 | 10/1993 |
| WO | A1-9319768 | 10/1993 |
| WO | 9611205 | 4/1996 |
| WO | A1-9611205 | 4/1996 |
| WO | 9840502 | 9/1998 |
| WO | A1-9840502 | 9/1998 |
| WO | 0015824 | 3/2000 |

OTHER PUBLICATIONS

Verma, Nature, vol. 389, 239–242, 1997.*

* cited by examiner

*Primary Examiner*—Dave T. Nguyen
(74) *Attorney, Agent, or Firm*—Birch, Stewart, Kolasch & Birch, L.L.P.

(57) ABSTRACT

The present invention relates to a novel method of genetic modification, wherein a nucleic acid of interest is transferred across a biological membrane, and/or directed to a specific location within or on a cell, by use of a synthetic transport entity. The transport entity according to the invention is new as such and produced by coupling a functional element (FE), such as a nuclear localization signal (NLS), an antennapedia peptide of a protein comprising both membrane translocation and nuclear transport properties, to a binding element (BE), such as a peptide nucleic acid (PNA), preferably separated by a linker molecule, which combination is then hybridized to a BE target sequence present on a carrier, which also includes the nucleic acid of interest. The present nucleic acid of interest may for example be a gene encoding a peptide, a protein or an RNA, or any other nucleic acid useful in genetic recombination events.

31 Claims, 6 Drawing Sheets

Figure 5
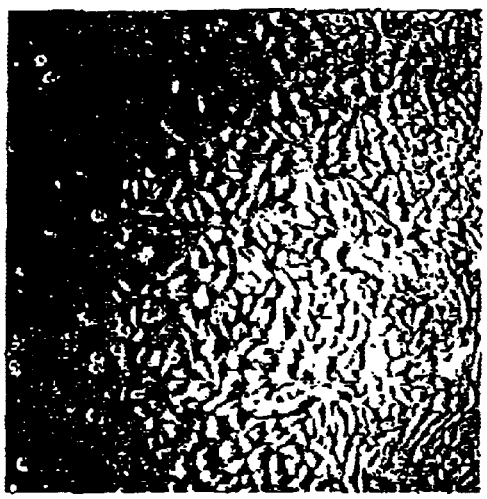
a.
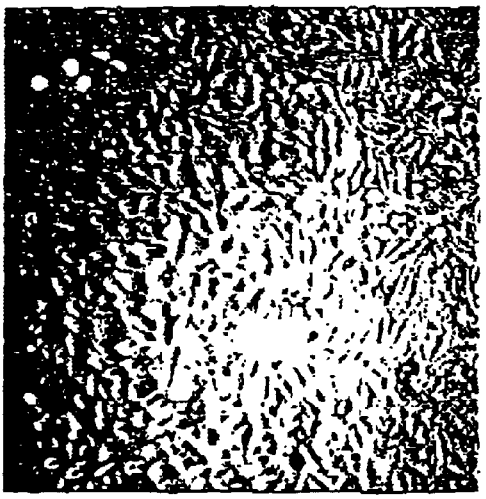
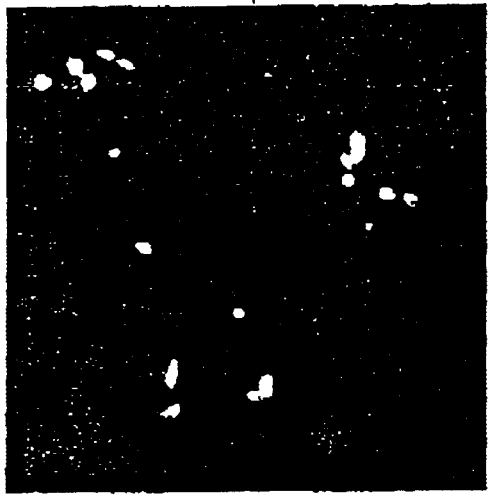
b.
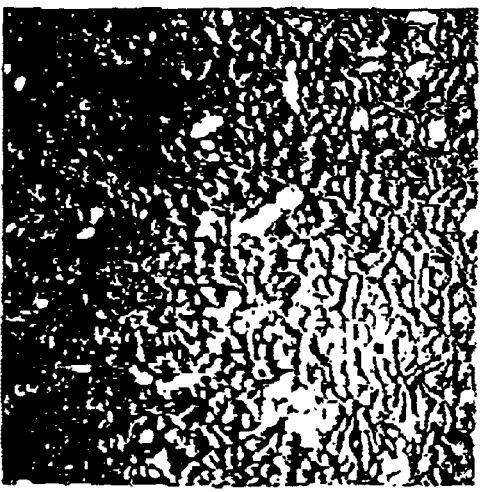
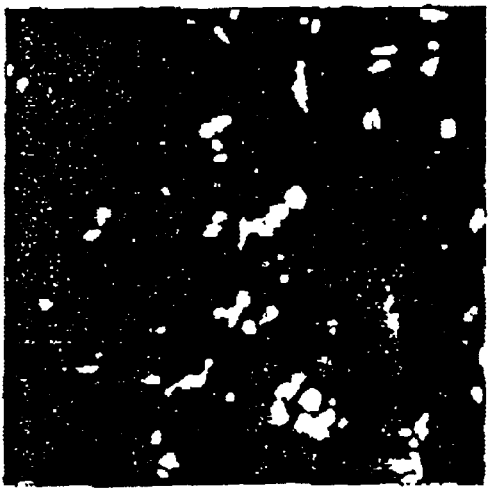
c.

TRANSFER METHOD FOR SPECIFIC CELLULAR LOCALIZATION OF NUCLEIC ACIDS

This application is the national phase under 35 U.S.C. §371 of PCT International Application No. PCT/SE99/00398 which has an International filing date of Mar. 15, 1999, which designated the United States of America.

TECHNICAL FIELD

The present invention relates to a method for transferring a nucleic acid, a derivative or an analogue thereof across a biological membrane, and/or directing it to a specific location within or on a cell, by use of a novel synthetic transport entity.

BACKGROUND

Methods for genetic modification, wherein exogenous genetic material is introduced into host cells to provide a function thereof, are usually limited by the rate of the uptake of the genetic material introduced into the cells. In eucaryotic cells, the nuclear uptake is often limiting. Even though direct injection methods have been used in this context, they are, however, extremely slow and labor-intensive. Thus, for use in larger scales, standard methods for transferring nucleic acids into cells are rather based on an uptake of complexes formed between different chemical compounds of nucleic acids. The genetic material is then left to enter the nuclei of the cells passively.

Nuclear localization signals (NLS) have been proposed in this context. As one example, Sebestyen et al. (Nat. Biotechnol, 1998, January; 16:(1):80–85) have suggested to use digitonin permeabilized cells to enable nuclear translocation after chemically linking an NLS peptide to a plasmid.

Further, Yoneda et al. (Exp. Cell. Res. 201:213 (1992)) have reported translocation of proteins larger than 970 kDa into the nucleus. More specifically, a fusion protein containing a nuclear localization signal (NLS) is transported into the nucleus of a cell.

U.S. Pat. No. 5,539,082, in the name of Nielsen et al, discloses a class of compounds known as peptide nucleic acids (PNAs). The PNAs described therein may comprise ligands, such as DNA bases, conjugated to a peptide backbone through a suitable linker. The PNAs according to U.S. Pat. No. 5,539,082 may e.g. be exploited to target specific genes and viruses within a cell, while the properties thereof are characterised by an absence of charge and a water solubility.

Further, WO 96/11205, also in the name of Nielsen et al, proposes a PNA conjugate comprised of a PNA chemically bound to a conjugate, such as any one of a large number of molecules, all of which are aimed at providing the PNA with desired properties. Accordingly, the PNA is useful as such, for example as a diagnostic or therapeutic agent. Said PNA is, similar to the above discussed U.S. Pat. No. 5,539,082, intended for exerting its advantageous functions within a cell.

SUMMARY OF THE PRESENT INVENTION

The object of the present invention is to provide a general and efficient method of genetic modification, wherein a nucleic acid of interest, a derivative or an analogue thereof is transferred across a biological membrane, and/or directed to a specific location within or on a cell, by a novel synthetic transport entity. The present transport entity is according to the invention provided by coupling a functional entity (FE), which may represent any kind of desired biological property, to a binding element (BE), such as a peptide nucleic acid (PNA), optionally with a linker molecule for keeping said FE and BE apart; and hybridisation thereof to a BE target present on a carrier of the nucleic acid of interest. The invention also relates to the novel transport entity as such as well as to various advantageous uses thereof.

BRIEF DESCRIPTION OF THE DRAWINGS

FIG. 5 illustrates the effect of a transport entity according to the invention: The effect of PNA-NLS when hybridised to PNA target containing EGFP plasmids and the effect of removing the excess PNA-NLS molecules from the transfection mix are shown.

DEFINITIONS

Figure 1:
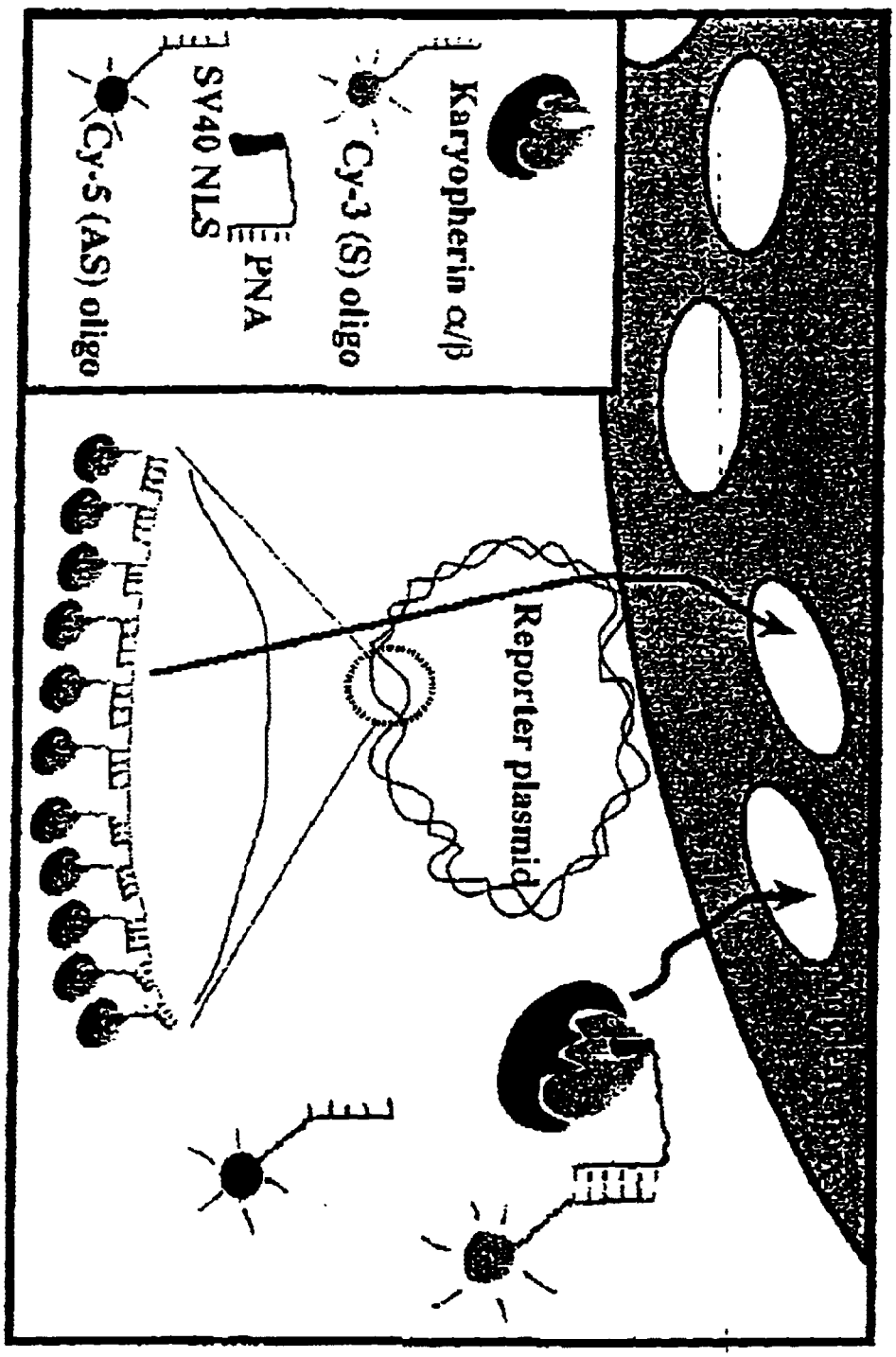
FIG. 1 is a schematic representation showing the target site in the anti-sense Cy-5 oligonucleotide hydridising to a sense PNA-NLS dual function peptide according to the invention.

In the present specification, the following terms and abbreviations are used as follows:

As used herein, the term "a nucleic acid of interest" relates to any DNA, RNA or other nucleotide, or any analogue or derivative thereof, useful to perform a genetic modification of a cell. In other words, it may be desired either to transfer such a "nucleic acid of interest" across a biological membrane, into a cell or a cell nucleus, and/or to direct said "nucleic acid of interest" to a specific location in such a new environment. A "nucleic acid of interest" may for example be a gene encoding a peptide or a protein, such as en enzyme, provide a regulating function, such as a binding site, etc.

The term "functional element" (FE) relates to any moiety capable of conferring one or more specific biological functions or properties to a molecule linked to it. It may e.g. provide a transporting capability. The present functional elements will be further examplified in the following detailed description of the invention.

A "binding element" (BE) may be any natural or synthetic nucleic acid, nucleic acid derivative or nucleic acid analogue capable of specific, strong and durable binding to a specified target thereof, preferably by hybridisation. One example of such a BE is the PNA described below.

Thus, a "PNA" refers to a Peptide Nucleic Acid and more specifically a DNA mimic with a pseudopeptide backbone consisting of aminoethyl glycine units, to which the nucleobases are attached via methylene carbonyl linkers. (See e.g. Nielsen, P. E. Peptide nucleic acid (PNA): "A lead for gene therapeutic drugs", *Perspectives in Drug Discovery and Design*, Vol. 4, pp. 76–84; and Dueholm of al., *New J. Chem.*, 1997, 21, 19–31: "Chemistry, properties and applications of PNA".) A PNA molecule is capable of hybridising to complementary ssDNA, dsDNA, RNA and PNA targets.

In the present patent application, it is to be understood that the term "PNA" refers to any DNA analogue comprised of the above mentioned backbone and nucleobases, and the term should thus not be limited to the specific structures disclosed in the reference given herein.

"NLS" refers to a nuclear localization signal, which may be any protein/peptide that recognizes and binds specifically to residues on certain transport proteins. More specifically, NLS domains are amino acid sequences which have evolved in poly-peptides, thereby facilitating migration of a polypeptide from the cytoplasm into the nucleus. Specified nuclear polypeptides containing NLS domains have been shown to enable the transport of a polypeptide-RNA complex into the nucleus (Mattaj and DeRobertis, 1985).

The term "vector" is used herein to denote a plasmid, an oligonucleotide, or any other molecule or construct capable of harbouring and/or transferring nucleic acids during genetic modification events. Thus, the term "vector" will also relate to any analogue or derivative of the ones exemplified above.

The term "cell wall" as used herein relates to any membrane that serves to surround a living organism, such as a eucaryotic cell membrane, the membrane surrounding a plant cell or a bacterium etc.

"Transfection" is used herein as a general term for any uptake by a cell of genetic material from the culture medium.

In the present context, a "transforming sequence" relates to any sequence that participates in a genetic modification event in a host cell, and may e.g. be a protein coding sequence, regulatory elements, an entire gene etc.

The term "recombinant" when referring to a cell is used herein simply to denote that a genetic modification has occurred therein. More specifically, it is used to indicate that a modification thereof has been obtained by the introduction of an exogenous nucleic acid, by the alteration of a native nucleic acid or that the cell is derived from a cell so modified.

The term "cell" or "host cell" is used herein to denote any cell, wherein any foreign or exogenous genetic material has been introduced. In its broadest sense, "host cell" is used to denote a cell which has been genetically manipulated.

The term "polymer", such as a "protein", "polypeptide" and "peptide", are used interchangeable herein and relates to any shorter or longer polymer of amino acid residues. In addition to naturally occurring amino acid polymers, the term also applies to amino acid polymers, wherein one or more amino acid residues are artificial chemical analogues of the corresponding naturally occurring amino acids. Further, the term "polymers" in the present context is also understood to include any glycoproteins, lipids, lipoproteins etc. useful for the herein disclosed purpose.

A "label" is a composition detectable by spectroscopic, photochemical, biochemical, immunological or chemical means.

The term "hybridise" refers herein to any binding, duplexing or hybridisation by base pairing of complementary bases of nucleic acids or peptide nucleic acids, or any derivatives or anaologues thereof.

The term "specific hybridisation" as used herein refers to the binding, duplexing or hybridisation of a molecule only to a particular nucleotide sequence when that sequence is present in a complex mixture or DNA and/or RNA, such as in a cellular environment.

As used herein, "homologous" sequences are sequences, which are identical or sufficiently similar to cellular DNA such that the targeting sequence and cellular DNA can undergo specific base pairing.

As used herein, a "targeting sequence" is a sequence, which directs the nucleic acid of interest to a desired site in a genomic or extra-chromosomal DNA or RNA-sequences contained in a target cell.

DETAILED DESCRIPTION OF THE INVENTION

In a first aspect, the present invention relates to a method of transferring a nucleic acid of interest across a biological membrane and/or directing such a nucleic acid to a specific location within or on a cell by use of a synthetic transport entity; which comprises the steps of (a) providing a carrier molecule comprising the nucleic acid of interest and a binding element (BE) target sequence, optionally as one element;

(b) providing a complex by coupling at least one functional element (FE) to a BE;

(c) hybridising the BE of said complex to the BE target of said carrier; and (d) contacting said transport entity with said biological membrane to provide for a transfer of the nucleic acid of interest across said membrane.

In a preferred embodiment of the present method, the binding element (BE) is a peptide nucleic acid (PNA) or a derivative or an analogue thereof capable of a specific and durable hybridisation to a PNA target sequence. The biological membrane may, for example, be a cell wall or a nuclear membrane. The complex created in step (b) may also comprise a spacer element, such as a linker (L) molecule, which separates the BE from the FE. In specific embodiments discussed in more detail below, the complex is comprised of more than one FE, in which case more than one linker may be used for separation. Step (a) may also include the insertion of a detectable marker or label in the carrier, which will facilitate a subsequent analysis of the efficiency of a genetic modification performed by this method.

Thus, in the present method, the advantageous properties of a binding element (BE), preferably a PNA or a PNA-like molecule, are primarily used in a first step of genetic transformation, preceding the actual transfer of a nucleic acid of interest into a cell or a nucleus, in which the effect of said nucleic acid of interest is desired. Thus, contrary to the prior art patents discussed in the introduction of the present specification, the advantage of the method according to the invention is not based, or relying, on the PNA's or binding element's capability to enter a cell or a nucleus. Rather, a PNA, or any equivalent binding element, is used according to the invention to provide a strong and satisfactorily coupling of an functional element (FE), via the PNA/PNA target interaction, to a carrier of a nucleic acid of interest. Thus, the FE will be used according to the invention to provide for the actual transport of the whole transfer entity across the biological membrane.

The PNA used in the preferred embodiment of the present method is a synthetic DNA analogue, that binds strongly to DNA and RNA with a higher affinity than DNA-DNA, RNA-DNA or RNA-RNA binding. The specific sequence thereof is designed in order to be specific for the nucleic acid to which it is intended to bind by hybridisation. PNA is metabolized very slowly and has also been shown to be non-toxic, which evidently is a great advantage when used in the pharmaceutical field. In addition, PNA is capable of a highly specific binding to the sequence of the nucleic acid that is complementary thereto, which in turn will provide a high frequency of correctly transformed cells when a PNA is used as BE in the present method for genetic transformation. Thus, the use of PNA as BE in the present method will confer excellent RNA and DNA hybridisation properties and biological stability to the complex formed. PNA is easily produced by someone skilled in this field by solid phase peptide synthesis (see e.g the international patent applications WO 95/01370 and WO 92/2072 and Nielsen, P. E.: Peptide nucleic acid (PNA): "A lead for gene therapeutic drugs", Perspectives in Drug Discovery and Design, Vol. 4, pp. 76–84).

In a preferred embodiment, the above mentioned linker sequence is essentially or completely uncharged. In this context, the term "non-reactive" is used to explain that the linker will not undergo any undesired or deleterious chemical reactions in the environment where it is used, e.g. that it does not react with any other components of the cell and/or nucleus that it contacts during a transfection process. It should also be essentially non-reactive as regards any reagents used in the present method as well as in view of the BE, such as PNA, and the functional element (FE), carrier etc. The present linker may e.g. be comprised of a polymer of a suitable number of amino acid residues, even though it is to be understood that any other molecule which functions as a spacer element without interfering with the desired result may be used. The size and nature of the linker sequence is dependent on the surrounding elements, as the primary function thereof is to provide a sufficient spacing between said elements to enable the effect of the desired function. Further, it should not interfere with the desired effect or expression of the nucleic acid of interest after transfer across the membrane.

In a specific embodiment, the present linker is cleavable by enzymes, such as cellular proteases or nucleases, enabling a transport across a biological membrane and/or adherence to a cell surface receptor, and then a subsequent disposal of the part or parts which are not desirable within the target, such as within the cytoplasm or the nucleus. In one particular embodiment, the BE is cleaved off, in order to provide for a more efficient effect of the inserted nucleic acid of interest. In another exemplary embodiment of the present method, the linker is capable of essentially hiding or masking the present transport entity, e.g. from undesired biological degradation, such as by proteases. In addition or alternatively, the linker may possess any further advantageous property, such as conferring another biological functional in itself.

The present functional elements (FEs) may provide any number of functions, such as a structural function, e.g. binding to a cell membrane target molecule, or an enzymatic function, e.g. an integrase activity, to enhance site-specific insertion of transferred DNA. Specific examples of advantageous FEs suitable for use according to the present invention are e.g. the function of cellular attachment, for example via transferrin receptors; cell membrane penetration, for example via antennapedia peptides; a nuclear transport, which will be discussed in more detail below; nucleic acid condensation peptides, preferably with strong, positive charge; endosome/lysosome escape, for example via adenovirus capsid proteins; and DNA integration, e.g. via an integrase. In one particular embodiment, the FE according to the invention is a protein of the HIV virus denoted TAT. In a another specific embodiment of the present method, the FE is an endosome disrupting component, which prevents degradation of the transferred biological element by the cellular process of lysosomal degradation.

In one embodiment of the present method, the biological membrane to be penetrated is the membrane or wall surrounding a eucaryotic or procaryotic cell. In an additional or alternative embodiment, the present method is used to insert a nucleic acid of interest into the nucleus of a eucaryotic cell. In the last mentioned embodiment, an efficient transport may be provided by creating a complex of a BE, such as a PNA, and a suitable nuclear localization signal (NLS) as the FE, or as a part of the FE.

In the present methods, a transport entity constituted of a BE and more than one of the mentioned FEs and linkers, in a suitable order, depending on the intended use and the desired result, may be used. Thus, as one example, a sequence of BE-linker-FE-linker-FE etc. may be used. Further, in a specific embodiment, the carrier will comprise more than one BE target sequence, thus enabling the hybridisation of more than one of the various BE-linker-FE complexes thereon. In this specific embodiment, there is no requirement that the BEs and/or FEs are identical. On the contrary, it may be advantageous to include different ones. Thus, in a specific embodiment, the complex may contain a PNA-linker-FE-linker-FE-sequence. The linkers are made to provide suitable spacings, depending e.g. on sizes and other properties of the elements. Further, the present carrier may include more than one target for a BE, such as PNA. Accordingly, such a carrier is capable of hybridisation to more than one of the herein exemplified complexes.

Further, the present invention relates to a method as disclosed above used for a diagnostic purpose. Thus, the nucleic acid of interest may encode a diagnostic marker or label and the method may be exerted in vivo, in order to enable a subsequent diagnosis of a subject in need thereof.

In addition, the present invention also relates to a kit suitable for performing any one of the methods disclosed herein. Such a kit may contain a binding element (BE), such as a PNA, or functional fragments thereof; a functional element (FE); such as a nuclear localization signal (NLS) or antennapedia peptide; a double-stranded oligonucleotide comprising target sites for said BE, such as a PNA target sequence. In one embodiment of the present kit, the FE enables the transfer and/or direction of the transport entity. In an alternative embodiment, the kit according to the invention also comprises suitable reagents for such transfer and/or direction. The kit according to the invention is presented in a suitable container, optionally containing instructions to facilitate the use thereof in appropriate methods.

In a second aspect, the present invention relates to a novel synthetic transport entity as such, which transport entity is useful in any one of the above discussed methods. The present BE-FE complex may be described by the general formula I:

$$\ldots \text{BE-L-FE} \ldots \tag{I}$$

wherein
  BE denotes a binding element;
  L denotes a linker, which however is an optional element; and
  FE denotes a functional element.
  Said complex is then capable of a sequence specific hybridisation to a BE target present on a carrier, which in addition to, or as a part of, the present BE, contains one or more nucleic acids of interest. The carrier may e.g. include a plasmid or a functional part thereof, such as a gene, an oligonucleotide, or a chimeraplast (see e.g. Cole Strauss, A., el al., in *Science*, vol 273, September 1996: "Correction of the Mutation Responsible for Sickle Cell Anemia by an RNA-DNA Oligonucleotide"). The BE may as mentioned above preferably be a PNA. The use of a linker according to the invention is optional, but preferred and it is described in detail above in relation to the first aspect of the invention.

Accordingly, one embodiment of this second aspect is a synthetic transport entity suitable for transporting a nucleic acid of interest across a biological membrane, such as a cell wall, and/or directing said nucleic acid to a specific location within, or on, a cell.

Further, in this second aspect of the invention, it is to be understood that the transport entity may include more than one of the mentioned FEs and linkers, in any suitable order, depending on the intended use and the desired result. Thus, in a specific embodiment, the complex may contain a BE-linker-FE-linker-FE-sequence. The carrier used is preferably a plasmid or an oligonucleotide which comprises one or more BE targets as well as one or more nucleic acids of interest. The strong sequence specific hybridisation of the BE/BE target will thus attach the complex to the carrier and the FE will preferably provide a transfer across the membrane in question. Linker molecules are included as appropriate.

Further, in another embodiment of this second aspect, the present invention relates to a transport entity especially suitable for transporting one or more nucleic acids of interest across a nuclear membrane of a eucaryotic cell, which is comprised of a BE, preferably a peptide nucleic acid (PNA), complexed with a FE which in this case comprises a nuclear localization signal (NLS). Thus, the present transport entity is particularly suitable for use in any method aimed at transfecting eucaryotic cells and directing nucleic acids of interest into the nucleus of the cell. However, depending on the particular BEs, FEs and nucleic acids chosen in each case, the present transport entity may be designed to enable an effective and specific transformation of any nucleus with any gene or genetic element.

Thus, more specifically, an advantageous embodiment of the second aspect is a PNA-NLS complex according to the invention, which is described by the general formula

... BE-L-FE ...                                   (I), wherein
the BE is a sequence of one or more PNA bases;
L denotes a linker sequence; and
the FE is an NLS sequence.

Said PNA-NLS complex is then hybridised to a plasmid containing a PNA target and a nucleic acid of interest, for example, a gene encoding a peptide, a protein, or an RNA. Said RNA may e.g. be a ribozyme, i.e. an RNA with enzymatic functions. In a specific embodiment, the NLS sequence is a SV40 large T antigen protein or a fragment thereof, which exhibits the desired nuclear localizing signal properties. However, as the skilled in this field will realize, the choice of a suitable NLS sequence will depend on the intended future use. Thus, the present NLS may be of any other origin or composition, as long as it fulfills the desired functions of transferring a transport entity according to the invention across the membrane and into the nucleus of the host cell.

In one specific and illustrating embodiment, the PNA-NLS complex according to the invention is described by formula III:

GCG CTC GGC CCT TTC (SEQ ID NO:1) L Pro Lys Lys Lys
    Arg Lys Val (SEQ ID NO:2) (III), wherein L is described by formula IV:

NHCH$_2$CH$_2$OCH$_2$CH$_2$OCH$_2$CO$_2$H                     (IV).

However, as the man skilled in the art will easily realise, variations may be made to these sequences while still providing an advantageous synthetic transport entity within the scope of the present invention as defined by the appended claims. Using the present invention, it is possible to mimic the different functions of viruses and microorganisms by attaching functions directly to a nucleic acid or any other biological molecule and/or complex to be transferred to a cell. At the same time, deleterious properties of native viral vectors are avoided by the use of the present transfer entity.

Thus, the PNA comprising complex used as illustrating the invention will provide excellent RNA and DNA hybridisation properties and biological stability and is easily produced by solid phase peptide synthesis (see e.g the international patent applications WO 95/01370 and WO 92/2072 and Nielsen, P. E.: Peptide nucleic acid (PNA): "A lead for gene therapeutic drugs", *Perspectives in Drug Discovery and Design,* Vol. 4, pp. 76–84).

More specifically, in the construction of the transfer entity according to the invention, the present complex and carrier are attached to each other by hybridisation of the BE of the complex to a BE target of the vector. Thus, in a particular embodiment, a PNA is hybridised to a PNA target sequence. Such a sequence specific hybridisation is easily performed by someone skilled in this field. (Hybridisation techniques are for example generally described in *"Nucleic Acid Hybridisation, A Practical Approach"*, Ed. Hames, B. D., and Higgins, B. D., IRL Press (1985); Gall and Pardue; *Proc. Natl. Acad. Sci. USA* 63: 378–383 (1969); and John et al., *Nature* 223:582–587 (1969)). Oligonucleotides may be prepared by any suitable method known to the skilled in this field, e.g. by direct chemical synthesis, such as the phosphotriester method of Narang et al., *Meth. Enzymol.* 68:90–99 (1979); the phosphodiester method of Brown et al., *Meth. Enzymol.* 68:109–151 (1979); the diethylphosphoramidite method of Beaucage et al., *Tetra. Lett.,* 22: 1859–1862 (1981); and the solid support method of U.S. Pat. No. 4,458,066.

Different vectors and nucleic acids for use in construction of the carriers are well known in the art and easily chosen by someone skilled. (For a general reference to laboratory procedures that may be used, see e.g. Sambrook et al., *Molecular Cloning, A Laboratory Manual, 2$^{nd}$* ed., vol. 1–3, Cold Spring Harbor Laboratory, Cold Spring Harbor, N.Y., 1989.)

In a specific embodiment of the transfer entity according to the invention, the carrier will also include a marker or a label, such as a fluorescent label, etc., to enable detection and identification of the cells that have included the entity. In case of a plasmid carrier, the label may e.g. be a gene encoding a fluorescent protein, such as a green fluorescent protein (GFP). In case of an oligonucleotide carrier, the marker is e.g. a fluorescent marker, such as Cy-3. Labelling and the detection thereof are well known to the skilled in this field and are e.g disclosed in U.S. Pat. Nos. 3,817,837; 3,850,752; 3,939,350; 3,996,345; 4,277,437; 4,274,149; and 4,366,241.

Using the novel transfer entity according to the last mentioned embodiment of the invention, any nucleic acid sequences of interest, such as genes, may be introduced efficiently into a host cell due to the NLS ability to enter the nucleus. The transfection entity according to the invention with its advantageous combined capability of efficient and specific transfer of genetic elements is of great value in many different applications, some of which will be disclosed in more detail below.

As illustrating the present invention, a method of transforming a cell may be described by the following steps:
   (i) providing a complex according to the invention by hybridising a carrier comprising at least one PNA target to the PNA domain of a PNA-NLS conjugate;
   (ii) contacting the complex formed in step (a) with a cell to be transfected in the presence of a transfection reagent;
   (iii) allowing the complex to enter the the nucleus of the cell; and
   (iv) allowing genetic transformation to take place, wherein the PNA complex is used as a the nuclear translocation initiator. Thus, any transforming sequences, which previously have been included in the vector on the requisite locations, may be transferred efficiently due to the NLS ability to enter the nucleus of the cell and the PNA ability to specifically bind to a PNA target on a vector which includes a nucleic acid sequence of interest.

As regards step (i), a variety of hybridisation formats is known to those skilled in this field, such as sandwich assays and competition or displacement assays. Hybridisation techniques are for example generally described in "*Nucleic Acid Hybridisation, A Practical Approach*", Ed. Hames, B. D., and Higgins, B. D., IRL Press (1985); Gall and Pardue; *Proc. Natl. Acad. Sci.* USA 63: 378–383 (1969); and John et. al., *Nature* 223:582–587 (1969).

Accordingly, firstly, the present method utilizes the transport capability of the NLS, whereby it is brought into the nucleus of the host cell together with any elements bound thereto. Once inside the nucleus, the NLS-protein complex may be dissolved and the protein partner to the FE (NLS) may exit the nucleus, while the transported carrier plasmid remains therein. Thus, secondly, the nucleic acid of interest present on the carrier may be utilised to perform a genetic transformation inside the target cell. Meanwhile, the protein partner to the FE (NLS) is able to repeat its functions by accompanying additional entities into the nucleus, thus contributing to the surprisingly high transformation frequence obtained according to the present invention.

Thus, as mentioned above, Sebestyen et al. used a chemical coupling of a nuclear localization signal to plasmids in methods of genetic modification of cells, wherein no PNA is used. However, it appears that their method includes the serious drawback of also impairing the plasmid function. Thus, there are essential differences in methods between Sebestyen et al. and the present invention, which may be a possible explanation to the substantial differences in transformation frequency obtained.

Thus, in a specific embodiment, the transfection reagent is a polymer transfection reagent, such as PEI (polyethylene imine). PEI has previously been used in gene therapy experimental set-ups and has been reported to be non-toxic in relevant dosages as well as capable of providing a high transfection efficiency. The pathway for PEI transfection is different from the standard lipid based transfection reagents commonly used today. The polymer functions as a proton acceptor and is believed to disrupt the endosomes by osmotic stress, thus releasing nucleic acids. In this context, it is to be noted that in other embodiments of the invention, using other specific functional elements, such transfection agents as PEI, lipids etc, may be excluded. This depends on whether or not the functional elements included in the transport entity are capable of providing a transport across the desired membrane. In a specific embodiment of the invention, the method according to the invention further comprises an additional step (v), wherein the resulting transformation is confirmed by measuring a previously included label or marker. The nature and identity of such labels and markers are also discussed elsewhere in this application.

In one advantageous embodiment of the above disclosed method according to the invention, the transformation defined in step (iv) introduces one or more protein coding sequences by use of a plasmid vector. Thereby, an efficient transformation yielding a host cell expressing e.g. an exogenous, or non-native, protein or polypeptide is obtained. In an alternative embodiment of the invention, the transformation according to step (iv) may be used to introduce one or more gene regulatory sequences in the host cell, whereby an otherwise silent gene may be expressed. This latter embodiment uses a technique known as gene activation, which is described in detail e.g. in U.S. Pat. No. 5,641,670. In either one of the two above disclosed embodiments of the present method, the resulting transformed cell may be used to produce substances such as proteins useful as medicaments.

In a further embodiment of the present method, the transformation defined in step (iv) is aimed at repairing a mutation in the host cell, which e.g. may be obtained by base specific DNA repair. In an alternative embodiment, said transformation is aimed at introducing a mutation in a host cell. This may be desired, e.g. if the expression of a gene is not desired due to the nature of the expression product or in the production of animal models for the study of various genetic diseases.

A further advantage of the present invention is that the illustrating PNA-NLS complex has a broad applicability and therefore the present invention may be used to transport more than 90% of all the plasmids conventionally used on an everyday basis in research laboratories worldwide.

Accordingly, another aspect of the present invention is a recombinant cell produced by a method as disclosed above. The invention also relates to animal models, such as mice, produced by a method according to the invention specifically designed for the study of certain genomic defects. General cloning techniques and methods of culturing cells are well known to someone skilled in this field. (See e.g. Sambrook et al., Molecular Cloning, A Laboratory Manual, $2^{nd}$ ed., vol. 1–3, Cold Sprig Harbor Laboratory, Cold Spring Harbor, N.Y., 1989; Freshney: Culture of Animal Cells, A Manual of Basic Technique, $3^{nd}$ ed., Wiley-Liss, New York, N.Y. (1994)).

One particularly advantageous aspect of the present invention is the use of the PNA-NLS complex and the transfection method disclosed above in gene therapy. For such an application, the conjugate may be hybridised to an oligonucleotide vector, such as a chimeric construct of DNA-RNA, PNA-DNA or any other combination. Gene therapy procedures have been used to correct acquired and inherited genetic defects in a number of contexts. The ability to express artificial genes in humans, or animals, such as mammals, facilitates the prevention and/or cure of many important diseases, often not amenable to treatment with other therapies. However, presently available approaches to gene therapy make use of infectious vectors, such as retroviral vectors, which include the genetic material to be expressed. Such approaches have limitations, such as the potential of generating replication-competent virus during vector production; recombination between the therapeutic virus and endogenous retroviral elements, potentially generating infectious agents with novel cell specificities; host ranges, or increased virulence and cytotoxicity; independent integration into large numbers of cells, increasing the risk of tumorigenic insertional event; limited cloning capacity in the retrovirus (which restricts therapeutic applicability) and short-lived in vivo expression of the product of interest. Thus, the use according to the present invention, wherein the PNA-NLS conjugates or complexes according to the invention are used, avoids the limitations and risks associated with the virus methods of the prior art. For example, previously, in the context of cystic fibrosis, adenovirus vectors have been used as a vector in gene therapy. Such a vector may give rise to undesired and immunological responses, which accordingly will be avoided by the advantageous use of the novel PNA-NLS conjugate according to the invention.

Consequently, the invention also relates to gene therapy methods as such, wherein conjugates or complexes according to the invention are used, in certain applications together with at least one transfection reagent, such as the above described polyethylene imine (PEI). Such methods are often aimed at repairing a mutated or defect gene, but may also be utilized to introduce a mutation, e.g. to prevent the expression of an undesired protein or to produce an animal model for the study of a certain defect. One example of a disease that may be treated by gene therapy is cystic fibrosis, CF, which afflicts a large number of patients. CF may be amenable to plasmid mediated gene transfer, as the target organ is the lung which is fairly accessible. However, as the number of diseases for which a genetic defect is identified steadily increases, it is predicted that in the future, a large number of additional gene related conditions or sicknesses will be identified as highly suitable for treatment by gene therapy according to the present invention. (For a general review of gene therapy methods, see e.g. Anderson, *Science* (1992) 256:808–813; Nabel and Felgner (1993) TIBTECH 11: 211–217; Mitani and Caskey (1993) TIBTECH 11:162–166; Mulligan (1993) *Science* 926–932; Dillon (1993) TIBTECH 11:167–175; Miller (1992) *Nature* 357:455–460; Van Brundt (1988) *Biotechnology* 6(10):1149–1154; Vigne (1995) *Restorative Neurology and Neuroscience* 8: 35–36; Kremer and Perricaudet (1995) British Medical Bulletin 51(1) 31–44; Haddada et al. (1995) in *Current Topics in Microbiology and Immunology*; and Yu et al., *Gene Therapy* (1994) 1:13–26.

A similar aspect of the present invention is the use of a transport entity or complex according to the invention to genetically modify cells to be used in cell therapy. (For a disclosure of the fundamentals of cell therapy methods, see e.g. Gage, F. H., *Nature,* vol. 392, Apr. 30, 1998.) Consequently, the invention also relates to such cell therapy methods as well as to cells used therein that have been genetically modified by a method according to the present invention.

Accordingly, in a last aspect, the present invention also encompasses methods of treatment, wherein an effective dose of the present transport entity is administered to a subject in need of treatment by gene therapy. Said treatment may be preventive and/or therapeutic, and it may be directed to any disease or condition. Such conditions include various genetic defects, but are not limited thereto. Rather, further conditions may also be contemplated, wherein it is desired to accomplish a change of the genetic environment, e.g. by insertion of a plasmid containing a gene encoding a desired therapeutical function. Details regarding such a treatment scheme will be determined by the attending physician in each case depending on such factors as the condition to be treated, age and weight of the patient etc. Pharmaceutical preparations suitable for use in such methods are also within the scope of the invention.

DETAILED DESCRIPTION OF THE DRAWINGS

FIG. 1 is a schematic representation showing the target site in the anti-sense Cy-5 oligonucleotide hydridising to a sense PNA-NLS dual function peptide according to the invention. The PNA-NLS/oligonucleotide complex binds to the karyopherine $\alpha/\beta$ proteins. The complex is then transported into the nucleus. Similarly the PNA target site was cloned into the EGFP plasmid allowing nuclear transport subsequent tp PNA-NLS hybridisation. Abbreviations: AS, anti-sense; S, sense; SV40 NLS, simian virus 40 nuclear localization signal; and PNA, peptide nucleic acid.

Figure 2:
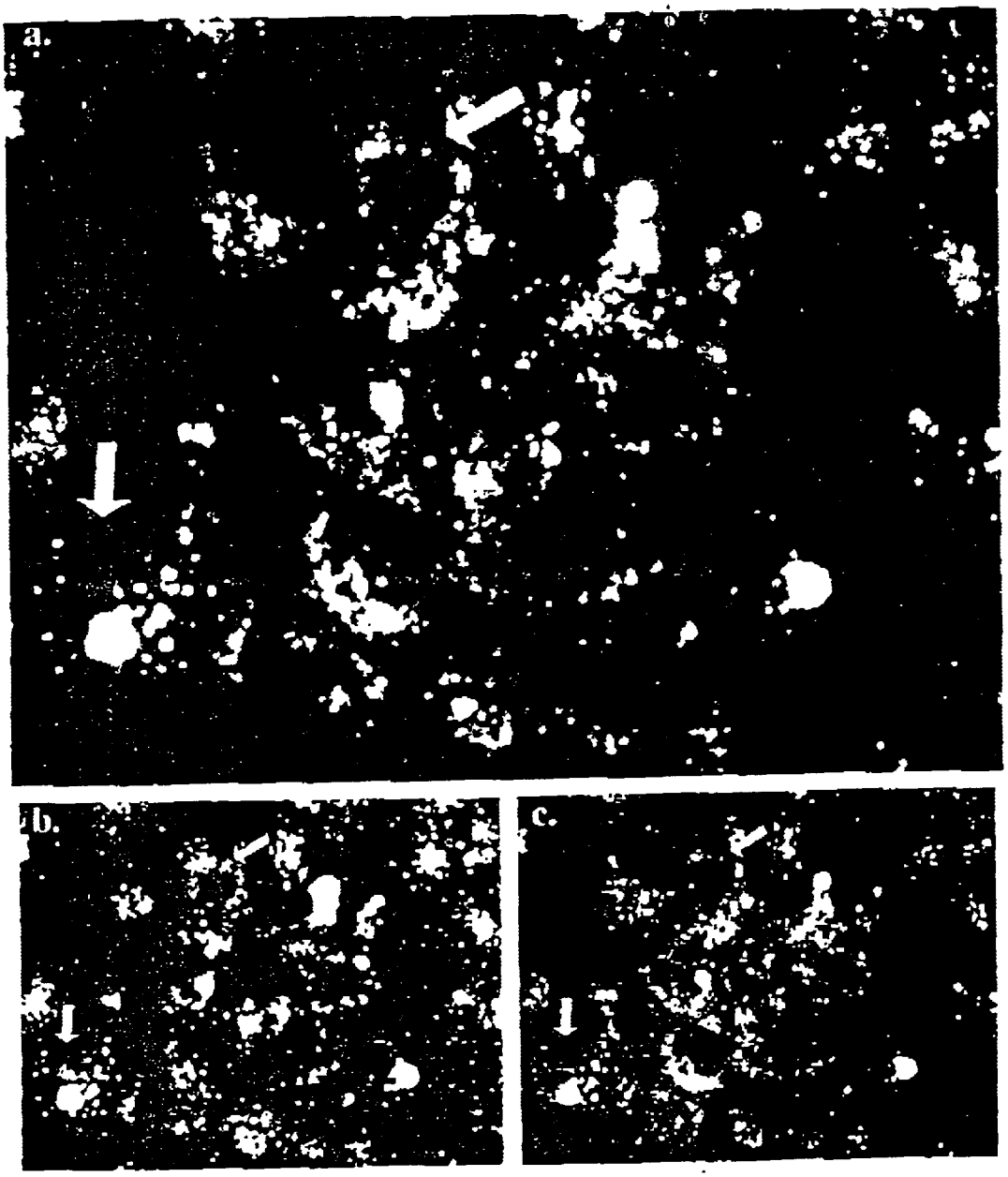
FIG. 2 illustrates nuclear translocation of fluorescence labelled oligonucleotides.

FIG. 2(*a*) illustrates nuclear translocation of fluorescence labelled oligonucleotides. Arrows denote nuclei where the Cy-5 oligo is enriched. FIG. 2(*b*) illustrates Cy-5 channel showing the location of Cy-5 AS-oligonuceotide. FIG. 2(*c*) illustrates Cy-3 channel showing the location of Cy-3 S-oligonucleotide.

Figure 3:
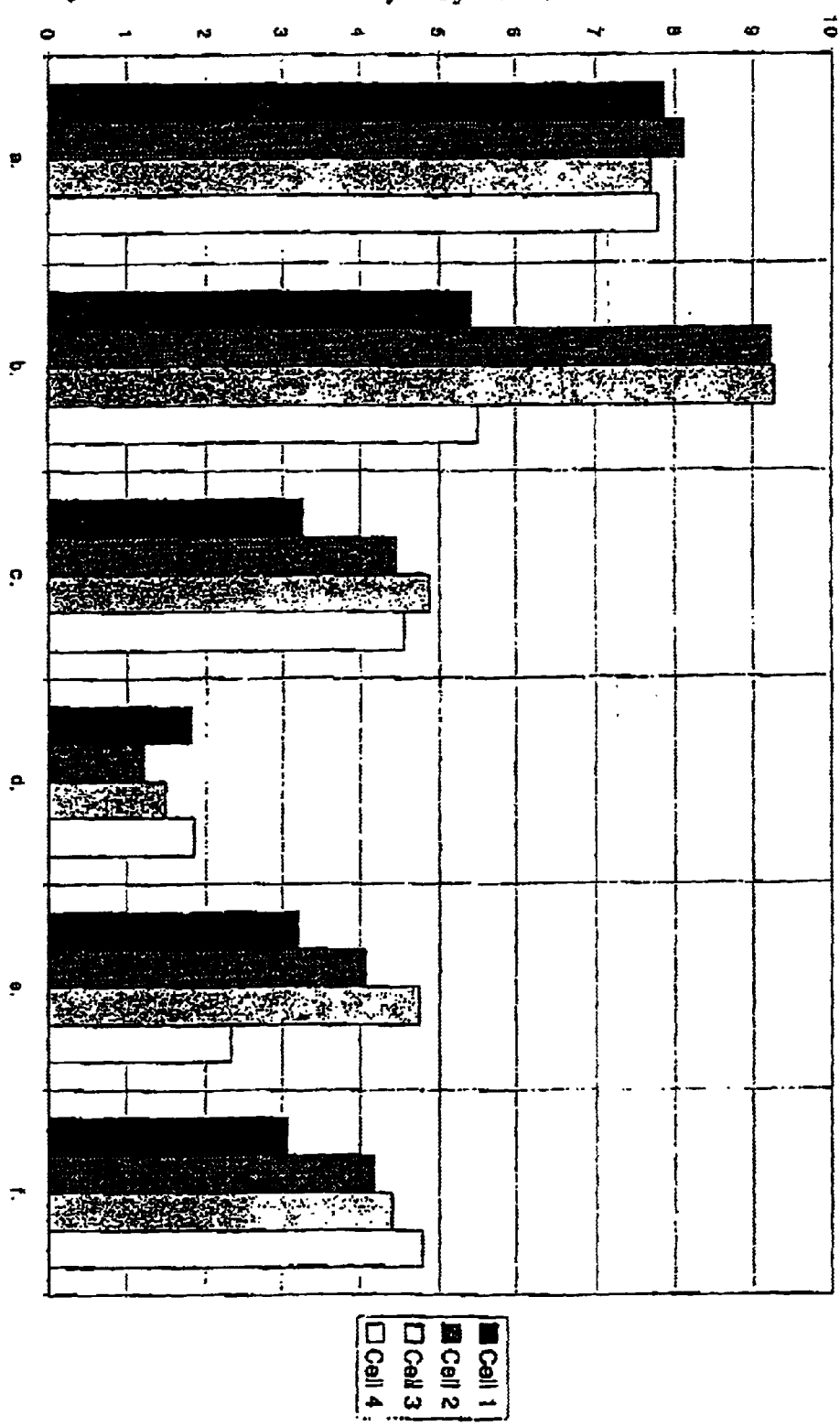
FIG. 3 shows nuclear, cytoplasmic and Golgi-like ratio of Cy-5/Cy-3 fluorescence.

FIG. 3 shows nuclear, cytoplasmic and Golgi-like ratio of Cy-5/Cy-3 fluorescence. (a) Anti-sense oligo, nucleus; (b) Anti-sense oligo, Golgi-like; (c) Anti-sense oligo, cytoplasm; (d) Sense oligo, nucleus (e) Sense oligo, Golgi-like; and (f) Sense oligo, cytoplasm.

Figure 4:
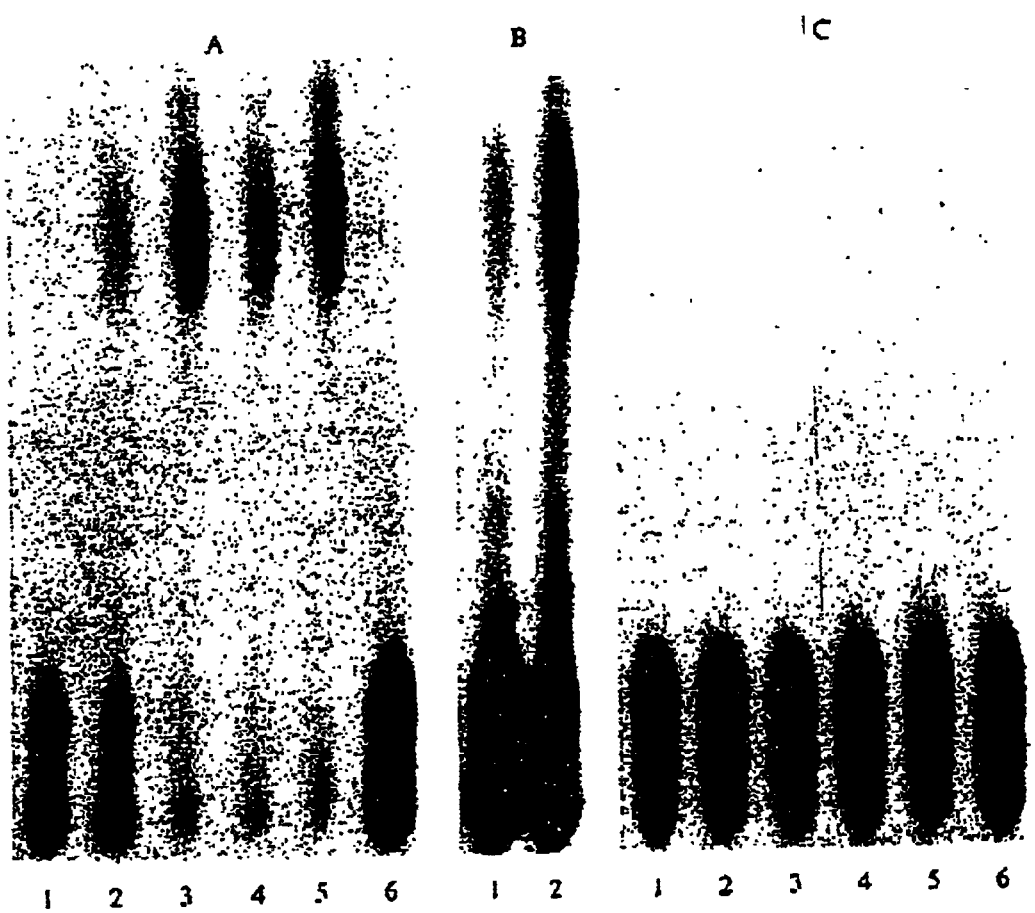
FIG. 4 is a shift assay of antisense and sense oligonucleotides with PNA-NLS dual function peptide according to the invention.

FIG. 4 is a shift assay of antisense and sense oligonucleotides with PNA-NLS dual function peptide according to the invention. (a) oligonucleotide with a target sequence (AS) for the PNA; (b) as in (a), but with prolonged exposure to show the weaker shift of the 1:10 hybridisation; (c) oligonucleotide without a target sequence (S) for the PNA. Oligonucleotide concentrations were 2.64 pmol in all lanes. PNA-NLS was added to 5'-labelled oligonucleotides at different molar ratios. Lane 1, 1:10; lane 2, 1:1; lane 3, 10:1; lane 4, 100:1; lane 5, 1000:1; and lane 6, 0:1.

FIG. 5 illustrates the effect of a transport entity according to the invention: The effect of PNA-NLS when hybridised to PNA target containing EGFP plasmids and the effect of removing the excess PNA-NLS molecules from the transfection mix are shown. (a) PNA target site containing EGFP plasmid transfected without PNA-NLS; (b) PNA target site containing EGFP plasmid hybridised to PNA-NLS in 1:100 ratio; (c) PNA target site containing EGFP plasmid hybridised to PNA-NLS in 1:100 ratio and with excess PNA-NLS removed before transfection.

Figure 6:
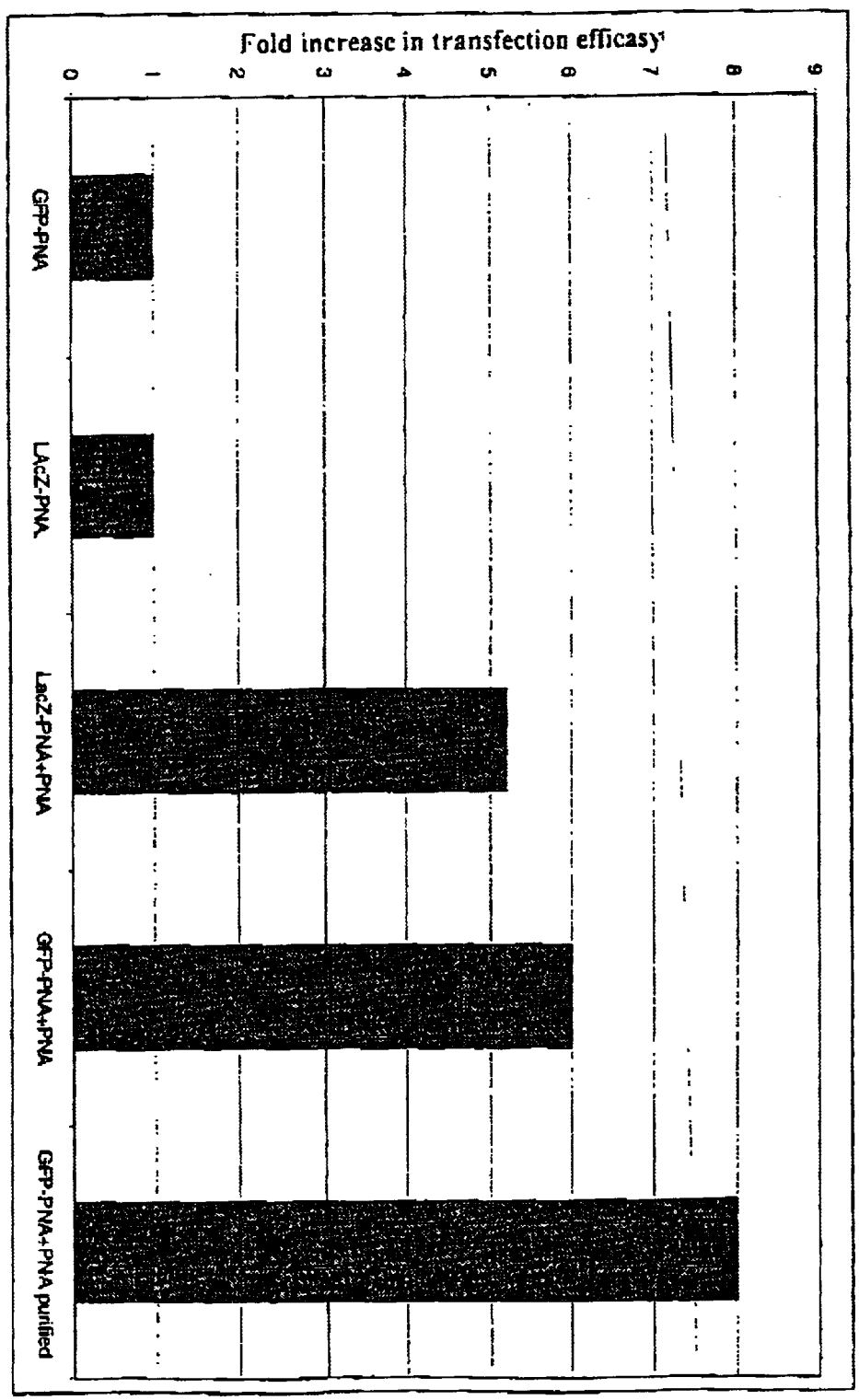
FIG. 6 shows lacZ and EGFP transfections with or without the addition of PNA-NLS and after purification of excess PNA-NLS.

FIG. 6 shows lacZ and EGFP transfections with or without the addition of PNA-NLS. EGFP transfections were also studied following removal of unbound PNA-NLS (purified).

EXPERIMENTAL

Below, the present invention, will be further disclosed by way of examples. It is to be understood that the examples are merely illustrating the invention and are not to be construed as limiting the scope of the invention as defined by the appended claims. All references below and elsewhere of this applications are hereby included herein by reference.
Materials and Methods
Cell Lines and Medium COS-7, 3T3 and HeLa cells were used for transfections and cultivated in DMEM, 4500 mg/l glucose, 10 mM L-glutamine, 10% fetal calf serum and 50 $\mu$g/ml gentamicine.
PNA-NLS The peptide nucleic acid (PNA) was synthesised at Perspective BioSynthesis Ltd. The sequence of the PNA was chosen with the criteria of being excluded from the plasmids as well as from known eucaryotic DNA sequences to avoid possible non-specific binding. The PNA peptides were attached with the hydrophobic spacer Fmoc-NC$_6$O$_3$H$_{11}$—OH (Fmoc-AEEA-OH) to a stretch of amino acid residues, PKKKRKV (SEQ ID NO:2), the SV40 core NLS. The complete sequence is GCGCTCGGCCCTTCC (SEQ ID NO:3)-linker-PKKKRKV (SEQ ID NO:2). Like peptides, PNA is synthesized on a polyethylene glycol-polystyren (PEG-PS) support with a peptide amide linker, the linker yielding a PNA amide upon cleavage of the final product (http://www.pbio.com/cat/synth/pna/pnacycle.htm).

Fluorochrome Labelled Oligonucleotides

Two fluorochrome labelled oligonucleotides were synthesised at Cybergene AB, AS-Cy-5 labelled, antisense to the PNA-NLS dual-function peptide, and S-Cy-3 labelled, sense to the PNA-NLS dual-function peptide. The oligonucleotides were HPLC purified. The Cy-3 and Cy-5 fluorochrome subunits for linking to the oligonucleotides were purchased from Perkin-Elmer.

Mobility Shift DNA-binding Assay Using Low Ionic Strength PAGE

Antisense- and sense-oligonuclecotides were end-labelled with T4-polynucleotide kinase using $\gamma$-$^{32}$P-ATP, >5000 mCi/mmol. The labelled oligonucleotides were incubated at room temperature with varying amounts of PNA-NLS. For separation of oligonucleotide/PNA-NLS complexes, 15%, low ionic-strength, non-denaturing polyacrylamide gel was used ("Mobility shift assay using low-ionic-strength PAGE", Short protocols in molecular biology, ed by Frederic M. Ausbel. Roger Brent, Robert E. Kingston, David D. Moore, J. G. Seidman, John A. Smith, Kevin Struhl, $2^{nd}$ ed, 1992).

Transfections with PNA-NLS and Fluorochrome Labelled Oligonucleotides

Transfections were made with 25 kDa PEI as follows. PNA-NLS:AS:S were mixed at a molar ratio of 1:1:1 and heated to 90° C. The mix was allowed to slowly cool to room temperature to obtain conditions for optimal hybridisation of PNA-NLS to the AS-oligo. The mix was diluted with water to a concentration of 0,05 $\mu$g/$\mu$l. To the mix of oligonucleotides and PNA-NLS, 1.44 $\mu$l of 0.1 M 25 kDa PEI solution was added per 2 $\mu$g nucleotide. The transfection solution was allowed to form complexes at room temperature for 10 minutes and was subsequently mixed with 1 ml DMEM with 10% bovine serum and 100 $\mu$g/ml gentamicin. The medium/transfection-complex mix was then added to the cells. For transfection, $10^5$ COS-7 cells were plated in 2 ml medium per well in 6-well plates 8 h prior to the transfection to allow for cell attachment. Incubation time for oligonucleotide transfections was 10 h. All incubations were made at 37° C. in 5% $CO_2$.

Transfections With PNA-NLS, EGFP and lacZ Plasmids

The plasmid EGFP-N3 (Enhanced Green Fluorescent Protein (Clonetech)) was modified to include the target sequence for the PNA-NLS hybrid. The EGFP-N3 plasmid was digested with AflII and ligated with a oligonucleotide fragment containing the PNA target sequence flanked by AflII sites. The fragment was cloned into a position outside any sequences known to be essential for EGFP gene function or plasmid function. Different clones of the construct were isolated containing different numbers of PNA target sites. Expression of the EGFP and lacZ genes gave information about the status of the plasmid in respect to functionality of the reporter gene as measured by directly scoring the number of positive cells. Transfections were made with 25 kDa PEI as follows. PNA-NLS:plasmid preparations were mixed at a molar ratio of 100:1 and heated to 90° C. The mix was slowly cooled to room temperature to allow for optimal hybridisation of PNA-NLS according to the invention to the plasmid target site. The mix was diluted to a concentration of 0.05 $\mu$g/$\mu$l. To the mix, 1.44 $\mu$l of 0.1 M 25 kDa PEI solution was added per 2 $\mu$g of plasmid. The transfection solution was allowed to form complexes in room temperature for 10 minutes and was subsequently mixed with 1 ml DMEM supplemented with 10% bovine serum and 100 $\mu$g/ml gentamicin. The transfection mix was then added to the target cells. The procedure for the lacZ plasmid was as above. For transfection, $10^5$ COS-7 cells were plated in 2 ml medium per well in 6-well plates. This was done 8 h prior to the transfection to allow for cell attachment. Incubation time was 48 h to allow for maximum gene expression. All incubations were made at 37° C. in 5% $CO_2$.

LacZ Staining

Transfected cells were fixed with 2% paraformaldehyde, 0.2% glutaraldehyde in 1×PBS. The staining solution, A, contained 5 mM potassium ferricyanide, 5 mM potassium ferrocyanide and 2 mM magnesium chloride. X-gal was dissoved in DMSO at a concentration of 40 mg/ml. Solution A was mixed with X-gal/DMSO solution at a 1:1 ratio, pre-warmed to 37° C. and added to the fixed cells. The cells were then incubated over night at 37° C. and scored in a light microscope.

Fluorescence Microscopy and Image Analysis

Fluorescence microscopy was performed on live cells in a Leica DMRXA microscope with a cooled frame CCD (Charge Coupled Device) camera. The subsequent image analysis was performed with the software Slidebook 2.1.4 from Intelligent Imaging Innovations Ltd. The increased nuclear uptake was calculated by masking the nucleus and then measure of the fluorescence from the Cy-5 (FIG. 2b) and the Cy-3 (FIG. 2c) spectra, respectively, and subtracting for the background fluorescence.

Results:

Nuclear Translocation of PNA-NLS Hybridised Oligonucleotides

In a first set of experiments, Cy-3 and Cy-5 fluorochrome labelled 15-mer oligonucleotides were hydridised to the PNA-NLS at a molar ratio of 1:1. The principle of this technique is schematically outlined in FIG. 1. After PEI mediated transfection an increased nuclear translocation of the Cy-5 fluorochrome labelled oligonucleotide/PNA-NLS complex by 200–800% (FIGS. 2,3) was observed as compared to the control Cy-3 fluorochrome labelled oligonucleotide. When analysed, the cells contained different levels of fluorescence in different cellular compartments. The level of fluorescence was similar in the nuclei of all positive cells. The cytoplasmic fluorescence varied from low to very intense. To verify that the PNA-NLS binds to the cognate sequence in the oligonucleotide, radiactivelly labelled oligonucleotides were incubated with PNA-NLS and separated on low-ion strength, non-denaturing polyacrylamide gels. As can be seen in FIG. 4, PNA-NLS binding was specific, as a shift was noticed using a molar ratio of 1:10 of PNA-NLS and the corresponding oligonucleotide, whereas a ratio of $10^4$:1 did not influence the oligo lacking the target site.

Nuclear Translocation of PNA-NLS Hybridised Plasmids

The PNA-NLS molecules were hybridised to PNA target sequence containing plasmids. LacZ or EGFP reporter constructs were used. The efficiency of gene transfer was measured as frequency of EGFP expressing cells or number of blue cells after staining for lacZ activity. PEI mediated transfection of a lacZ or EGFP plasmids was enhanced 3–8-fold by the addition of a 100:1 ratio of PNA-NLS peptide (FIGS. 5,6). The plasmids both contained 11 concatemeric PNA target sites cloned into a region without known function (located 3' of the poly-adenylation signal of the reporter gene). Initially dose-response analysis was carried out indicating that a 100:1 ratio of PNA-NLS:plasmid was optimal (data not shown). A lacZ plasmid containing 2 concatemeric PNA target sites did not differ from wild-type efficacy (data not shown) and was not further studied. The transfection efficacy was enhanced (8 fold as compared to control) when the plasmid-PNA-NLS complex was purified from free PNA-NLS as shown in the case of the EGFP plasmid (FIGS. 5,6). This indicates that free PNA-NLS blocked the nuclear transport of the plasmid/PNA-NLS complex thus impairing the nuclear translocation. When mixing a control plasmid with PNA-NLS, no effect could be seen on transfection efficacy. The plasmid/PNA-NLS interaction does not seem to disturb the normal functions of a marker gene as shown by the expression of the reporter gene in the complexes containing either lacZ or EGFP plasmids. Moreover, addition of 100-fold more free NLS peptide (ratio $10^4$:1 of NLS:plasmid) markedly reduced the transfection efficacy of plasmids containing the PNA site (not shown).

Discussion

The present invention demonstrates that a PNA molecule linked to an SV40 NLS peptide can work as a nuclear targeting signal when hybridised to a fluorescent labelled oligonucleotide or to a plasmid containing a reporter gene. Similar results were obtained using DOTAP or 25 kD PEI as transfection reagents in HeLa, NIH-3T3 or COS-7 cells, demonstrating the versatility of the technique (data not shown). The method according to the invention is of potential value for transfections in general and may also be applied in the context of gene therapy or DNA-vaccination. The increased uptake of nucleic acids into target cells may be vital for gene expression, as well as for the delivery of anti-sense constructs or mutation-inducing oligonucleotides. In the context of anti-sense activity it should also be possible to apply a PNA-NLS construct alone. According to the present invention, a PNA target sequence, CGCGAGC-CGGGAAGG (SEQ ID NO:4), was used, which does not exist in the unmodified EGFP or the lacZ plasmids that were studied. The interaction of PNA with its target sequence is highly specific and the PNA does not cross-hybridise to non-related sequences. The strong interaction between DNA and PNA also prevents the complex from dissociating (Knudsen H., Nielsen P. E.: Antisense properties of duplex- and triplex-forming PNAs, Nucleic Acids Research 24(3) 494–500 (1996)).

While the present invention was in progress, a report appeared in which digitonin permeabilized HeLa cells were used to study nuclear translocation after chemically linking the NLS peptide to a plasmid and injecting it into the cytoplasm (Sebestyen M. G, Ludtke J. J., Bassik M. C., Zhang G., Budker V., Lukhtanov E. A., Hagstrom J. E., Wolff J. A., DNA vector chemistry: The covalent attachment of signal peptides to plasmid DNA, Nature Biotechnology 16(1):80–5 (1998)). The results obtained by Sebestyen et al. also show increased nuclear import using NLS linked plasmids. However, due to the chemical modifications inherent to this technique expression from reporter genes in the modified plasmids was blocked. In contrast, using PNA-NLS peptides expression was maintained. To this end, the location of PNA target sites in a supposedly non-vital region might be essential. For plasmids, it was noted that two PNA target sites had no effect on transfection efficacy, whereas 11 sites markedly increased efficacy. Even though the present inventors did not study whether it is important to localize all target sites to the same region in the plasmid or whether they could be spread out evenly, both alternatives are within the scope of protection as defined by the appended claims. Moreover, extrapolating from the data of Sebestyen et al. (1998) it is proposed that a high local NLS concentration is essential, as these authors saw no effect using $\geq$115 NLS sequences per plasmid, whereas according to the present invention, an enhanced uptake was seen using a 250 bp concatemeric stretch harbouring 11 PNA-NLS target sites. However, it is not at present completely clear whether or not PNA-NLS sequences bind to each target site, and accordingly, this will have to be tested by the skilled in this field who uses the method according to the invention. The SV40 core NLS was chosen of practical reasons, since it is one of the most studied NLS sequences. SV40 linked proteins larger than 970 kDa have been reported to translocate into the nucleus (Yoneda Y., Semba T., Kaneda Y., Noble R. L., Matsuoka Y., Kurihara T., Okada Y., Imamoto N.: "A long synthetic peptide containing a nuclear localization signal and its flanking sequences of SV40 T-antigen directs the transport of 1 gM into the nucleus efficiently", Experimental Cell Research 201(2):313–20 (1992)). This should be compared with the molecular weight of the PNA target sequence containing EGFP plasmid of 2800 kDa. Furthermore, Zanta et al (Zanta M. A., Belguise-Valladier P., Behr J., Gene delivery: "A single nuclear localization signal peptide is sufficient to carry DNA to the cell nucleus", Proceedings of the National Academy of Sciences of the United States of America, 1999 96:91–96) disclosed, after the earliest priority date of the present patent application, an interesting paper wherein ligation of an NLS-DNA hybrid to a purified reporter gene fragment is used (8). The authors clearly demonstrate the feasibility of a NLS approach. However, the method used by Zanta et al. (supra) is more cumbersome than the present method, since it involves restriction enzyme cleavage of the plasmid and subsequent ligation of the NLS carrying oligonucleotide to the reporter gene fragment.

The present method and transport entity, such as the PNA-NLS system, will be efficient in assays and therapies involving transient transfections as well as in systems where repair constructs are shuttled into the nucleus for mutation repair. The system for nuclear translocation based on the SV40 core NLS seemed to be saturated as a plateau of nuclear fluorescence was reached using fluorochrome labelled oligonucleotides. This is indicated by the fact that different cytoplasmic levels of oligonucleotides still gave rise to similar nuclear levels of the targeted oligonucleotide, while the non-targeted oligonucleotide shows a relatively broad variation (FIG. 3b). Scoring of nuclear translocation of oligonucleotides with Cy-5 labelled anti-sense oligonucleotide allowed for objectivity because of the infrared emission of the Cy-5 fluorophore. The binding partner of SV40 NLS is karyopherin-$\alpha$ which subsequently forms a complex with karyopherin-$\beta$ (Miyamoto Y., Imamoto N., Sekimoto T., Tachibana T., Seki T., Tada S., Enomoto T., Yoneda Y., Differential modes of nuclear localization signal (NLS) recognition by three distinct classes of NLS receptors, Journal of Biological Chemistry, 272(42) :26375–81 (1997)). The total amount of NLS is of importance, and will be determined by the skilled in this field utilizing the present method, as this transport mechanism can be saturated (Michaud N., Goldfarb D. S., Most nuclear proteins are imported by a single pathway, Experimental Cell Research, 208(1):128–36 (1993)). Saturation of a nuclear import system is also the likely explanation for the findings according to the present invention that addition of free NLS impairs nuclear transport. To further enhance the nuclear import of oligonucleotides, a mixture of PNA-NLS peptides containing a set of NLS sequences targeting different NLS pathways could be employed (Michaud et al, supra). This will ensure that saturation of one pathway will not limit the nuclear translocation of the transfected biomolecules. To this end at least three different NLS receptor families have been reported as exemplified by: Qipl, Rch 1 and NPI-1 (Miyamoto el al., supra). According to the present invention, it is suggested that a way to mimic the lentivirus nuclear entry would be to bind the HIV-1 Matrix Association (MA) protein to the nucleic acid construct via a PNA-NLS peptide. The complex would then bind Vpr and might subsequently be processed as a pre-integration complex (Bukrinsky M. I., Haffar O. K., HIV-1 nuclear import: Matrix protein is back on center stage, this time together with Vpr. Molecular Medicine, 4(3):138–43 (1998)). The function of the MA-Vpr complex is proposed to be analogous to the extended SV40 NLS sequence described by Xiao et al. (1997) (Xiao C. Y., Hubner S., Jans D. A., SV40 large tumor antigen nuclear import is regulated by the double-stranded DNA-dependent protein kinase site (serine 120) flanking the nuclear localization sequence, Journal of Biological Chemistry, 272(35):22191–8 (1997)). In the prior art, proteins enhancing various aspects of nucleic acid delivery have been studied (Boussif O., Lezoualch F., Zanta M. A., Mergny M. D., Scherman D., Demeneix B., Behr J. P., A versatile factor for gene and oligonucleotide transfer into cells in culture and in vivo: polyethylenimine, Proceedings of the National Academy of Sciences of the United States of America 92(16):7297–301 (1995)). According to the present invention, it is suggested that such functions, in addition to the NLS-mediated transfer, could be directly targeted to the nucleic acid using the PNA approach.

What is claimed is:

1. A synthetic transport complex for transferring a nucleic acid of interest across a biological membrane into a cell, wherein the complex is comprised of two or more functional elements (FE), each of which is complexed to a binding element (BE) in the form of a peptide nucleic acid (PNA), and a nucleic acid carrier, which comprises at least two BE target sequences and a nucleic acid of interest in a vector; said carrier being hybridized to said complex using the BE-BE interaction.

2. The transport complex according to claim 1, wherein said two or more FEs provide different functions.

3. The transport complex according to claim 1, wherein said vector is a plasmid or an oligonucleotide.

4. The transport complex according to claim 1, wherein the carrier includes a detectable marker element.

5. The transport complex according to claim 1, wherein the nucleic acid of interest is a gene encoding a peptide, a protein or an RNA.

6. The transport complex according to claim 1, wherein said BE and FEs are separated by linker elements.

7. The transport complex according to claim 1, which comprises more than one FE-BE-complex, each one of which is hybridized to a separate BE target sequence present on the same carrier.

8. The transport complex according to claim 1, wherein the FE is a nuclear localization signal (NLS), or a fragment thereof exhibiting nuclear localizing signal properties.

9. The transport complex according to claim 1, wherein the FE is a protein exhibiting properties enabling both membrane translocation and nuclear transport.

10. A method for transferring a nucleic acid of interest across a biological membrane of a target cell comprising
administering to the cell the synthetic transport complex according to claim 1.

11. The method according to claim 10, wherein in said transport complex said two or more FEs provide different functions.

12. The method according to claim 10, wherein in said transport complex said BE and FEs are separated by linker element(s).

13. The method according to claim 10, wherein in said transport complex the carrier provided is a plasmid or an oligonucleotide vector comprising said nucleic acid of interest and at least one target sequence.

14. The method according to claim 10, wherein in said transport complex a detectable marker element is inserted in said carrier.

15. The method according to claim 10, wherein in said transport complex the nucleic acid of interest is a gene encoding a peptide, a protein or an RNA.

16. The method according to claim 10, wherein said complex comprises more than one FE-BE complex, each one of which is hybridized to a separate BE target sequence present on the same carrier.

17. The method according to claim 10, wherein the biological membrane is a cell wall.

18. The method according to claim 10, wherein the biological membrane is a nuclear membrane, and wherein at least one functional element (FE) of said two or more functional elements is a protein, which enables both membrane translocation and nuclear transport of the nucleic acid of interest.

19. The method according to claim 10, wherein in said transport complex the FE is a nuclear localization signal (NLS), or a fragment thereof exhibiting nuclear localizing signal properties.

20. The method according to claim 10, wherein in said transport complex the FE is a protein provided in said complex, which enables both membrane translocation and nuclear transport of the nucleic acid of interest.

21. A kit comprising components for making a transport entity capable of transferring a nucleic acid of interest across a biological membrane into a cell, which kit comprises at least two binding elements (BE) in the form of a peptide nucleic acid (PNA); two or more functional elements (FE); a plasmid containing said nucleic acid of interest; an oligonucleotide comprising a target for each of said BEs and being suitable for cloning in said plasmid; and optionally reagents suitable for such transfer.

22. The kit according to claim 21, wherein said two or more FEs provide different functions.

23. The kit according to claim 21, wherein at least one functional element (FE) is a nuclear localization signal (NLS), or a fragment thereof exhibiting nuclear localizing signal properties.

24. The kit according to claim 21, wherein the FE is a protein provided in said complex, which enables both membrane translocation and nuclear transport of the nucleic acid of interest.

25. The transport complex according to claim 8, wherein said NLS is a SV40 large T antigen protein.

26. The transport complex according to claim 9, wherein the FE is an HIV protein.

27. The transport complex according to claim 26, wherein said HIV protein is TAT.

28. The method according to claim 19, wherein in said transport complex said NLS is a SV40 large T antigen protein.

29. The method according to claim 20, wherein in said transport complex the FE is an HIV protein.

30. The method according to claim 29, wherein said HIV protein is TAT.

31. The kit according to claim 23, wherein said NLS is a SV40 large T antigen protein.

* * * * *

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Peptide Nucleic Acid linked to SEQ ID NO:2

<400> SEQUENCE: 1
gcgctcggcc ctttc                                                   15

<210> SEQ ID NO 2
<211> LENGTH: 7
<212> TYPE: PRT
<213> ORGANISM: Artificial Sequence
<220> FEATURE:
<223> OTHER INFORMATION: Nuclear Localizaiton Signals linked to SEQ ID
      NO:1

<400> SEQUENCE: 2

Pro Lys Lys Lys Arg Lys Val
1               5

<210> SEQ ID NO 3
<211> LENGTH: 14
<212> TYPE: DNA
<213> ORGANISM: Artificial Sequence
<220> FEATURE:
<223> OTHER INFORMATION: Peptide Nucleic Acid linked to SEQ ID NO:2

<400> SEQUENCE: 3
gcgctcggcc cttc                                                    14

<210> SEQ ID NO 4
<211> LENGTH: 15
<212> TYPE: DNA
<213> ORGANISM: Artificial Sequence
<220> FEATURE:
<223> OTHER INFORMATION: Peptide Nucleic Acid target sequence

<400> SEQUENCE: 4
cgcgagccgg gaagg                                                   15
```